United States Patent [19]

Hoffmann

[11] 4,330,482
[45] May 18, 1982

[54] PROCESS FOR THE PREPARATION OF HALOGENOALKENES

[75] Inventor: Hellmut Hoffmann, Wuppertal, Fed. Rep. of Germany

[73] Assignee: Bayer Aktiengesellschaft, Leverkusen, Fed. Rep. of Germany

[21] Appl. No.: 218,394

[22] Filed: Dec. 18, 1980

[30] Foreign Application Priority Data

Jan. 3, 1980 [DE] Fed. Rep. of Germany ....... 3000065

[51] Int. Cl.$^3$ .................... C07C 21/19; C07C 69/743; C07C 49/567; C07C 121/48
[52] U.S. Cl. ................................. 260/465 G; 260/404; 260/465.7; 560/8; 560/118; 560/124; 560/211; 564/180; 564/181; 564/188; 564/190; 564/205; 568/315; 568/347; 568/391; 570/200; 570/217
[58] Field of Search ................... 560/8, 124, 118, 211; 260/464, 465 G, 465.7; 564/190, 205; 568/315, 347, 391; 570/200, 217

[56] References Cited

U.S. PATENT DOCUMENTS 4,157,447 6/1979 Engel ..................................... 560/8

FOREIGN PATENT DOCUMENTS 2917620 11/1980 Fed. Rep. of Germany .

Primary Examiner—Dolph H. Torrence
Attorney, Agent, or Firm—Sprung, Horn, Kramer & Woods

[57] ABSTRACT

In the process for the production of a halogenoalkene of the formula

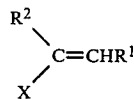

in which
$R^1$ is an optionally substituted alkyl, alkenyl, alkinyl, cycloalkyl, cycloalkenyl, aralkyl, aralkenyl or aryl radical or an optionally substituted heterocyclic radical, $R^2$ represents a halogen atom, a cyano group, an optionally substituted alkyl, alkenyl, alkinyl, cycloalkyl, aralkenyl, aryl, alkylcarbonyl, arylcarbonyl, alkoxycarbonyl or aminocarbonyl radical or an optionally substituted heterocyclic radical, and X is a halogen atom, in which an α-hydroxy-phosphonic acid ester of the formula

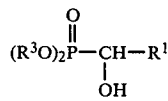

in which
$R^3$ each independently is an alkyl or phenyl radical, or the two radicals $R^3$ together are an alkanediyl (alkylene) radical, is reacted with a phosphorus-containing olefinating agent of the formula

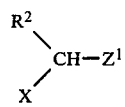

in which
$Z^1$ is the phosphorus-containing radical

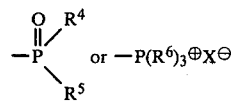

$R^4$ and $R^5$ each independently is an alkyl, phenyl, alkoxy or phenoxy radical or together are an alkanedioxy radical, and
$R^6$ is an alkyl or phenyl radical, in the presence of a base at a temperature between about $-70°$ and $+150°$ C., the improvement which comprises effecting the reaction in the presence of a halogen carrier. The end products are useful as intermediates such as in synthesizing pyrethroid-like insecticides.

10 Claims, No Drawings

PROCESS FOR THE PREPARATION OF HALOGENOALKENES

The invention relates to an unobvious process for the production of halogenoalkenes, some of which are known.

It is known that certain halogenoalkenes, such as 3-(2-chloro-2-phenyl-vinyl)-2,2-dimethyl-cyclopropane-1-carboxylic acid ethyl ester, are obtained when phosphonic acid esters, such as benzylphosphonic acid diethyl ester, are treated with strong bases, such as butyl-lithium, and the ylides intermediately formed are reacted with halogen carriers, such as carbon tetrachloride, and the products are then reacted with oxo compounds, such as 3-formyl-2,2-dimethyl-cyclopropane-1-carboxylic acid ethyl ester (see U.S. Pat. No. 4,157,447).

However, to carry out this preparation process for halogenoalkenes would require great technical effort.

The strong bases, such as butyl-lithium, required for forming ylides from phosphonic acid esters are sensitive to moisture and air; the reaction is therefore carried out in an inert gas atmosphere, for example under nitrogen or argon, and using an inert, carefully dried diluent. Since the reaction has to be carried out at a low temperature, for example at −70° C., it is also necessary for the reaction mixture to be intensively cooled. Working up the reaction mixture to isolate the desired products, which are obtained as isomer mixtures, is likewise expensive; it comprises several extractions and solvent distillations and a chromatographic separation process. For these reasons, the known synthesis method is not very suitable for preparation of halogenoalkenes such as 3-(2-chloro-2-phenyl-vinyl)-2,2-dimethyl-cyclopropane-1-carboxylic acid esters on an industrial scale.

In our prior copending application Ser. No. 140,644, filed Apr. 16, 1980 (corresponding to German Patent Application Ser. No. P29 17 620.3) alkenes are disclosed as being obtained by reacting α-hydroxyphosphonic acid esters with phosphorus-containing olefinating agents.

The present invention now provides a process for the production of a halogenoalkene of the general formula

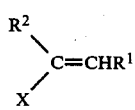  (I)

in which
$R^1$ represents an optionally substituted alkyl, alkenyl, alkinyl, cycloalkyl, cycloalkenyl, aralkyl, aralkenyl or aryl radical or an optionally substituted heterocyclic radical,
$R^2$ represents a halogen atom, a cyano group, an optionally substituted alkyl, alkenyl, alkinyl, cycloalkyl, aralkenyl, aryl, alkylcarbonyl, arylcarbonyl, alkoxycarbonyl or aminocarbonyl radical or an optionally substituted heterocyclic radical and
X represents a halogen atom,
in which an α-hydroxy-phosphonic acid ester of the general formula

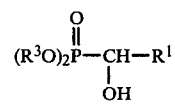  (II)

in which
$R^1$ has the meaning indicated above and
$R^3$ represents an alkyl or phenyl radical, or the two radicals $R^3$ together represent a straight-chain or branched alkanediyl (alkylene) radical,
is reacted with a phoshorus-containing olefinating agent of the general formula

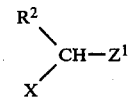  (III)

in which
$R^2$ and X have the meanings indicated above and
$Z^1$ represents a phosphorus-containing radical

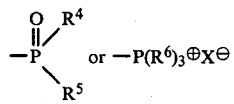

in which
$R^4$ and $R^5$ are identical or different and individually represent an alkyl, phenyl, alkoxy or phenoxy radical or together represent an alkanedioxy radical,
$R^6$ represents an alkyl or phenyl radical and
X represents a halogen atom,
in the presence of a base, optionally in the presence of catalysts, and optionally using diluents, at a temperature from about −70° to +150° C., characterized in that the reaction is carried out in the presence of a halogen carrier.

Surprisingly, alkenes of the formula (I) can be obtained in good yields and in a high purity by the new process, which is simple and inexpensive to carry out and for which starting compounds which can be prepared without great effort are to be employed.

Examples of further advantages of the new process are the possibility of carrying out the reaction at room temperature or at least at temperatures which do not deviate far from room temperature, the possibility of using inexpensive bases, such as alkali metal hydroxides or alcoholates, and the possibility of employing water-containing solvents.

A particular advantage of the process according to the invention is that the preparation of aldehydes, which are in general employed as reactants in the preparation of alkenes by reaction of carbonyl compounds with phosphorus-containing olefinating agents, can be avoided.

If, for example, α-(3-methoxy-carbonyl-2,2-dimethyl-cycloprop-1-yl)-α-hydroxy-methane-phosphonic acid dimethyl ester and α-chlorobenzylphosphonic acid diethyl ester are used as starting substances, the reaction, according to the invention, is illustrated by the following equation:

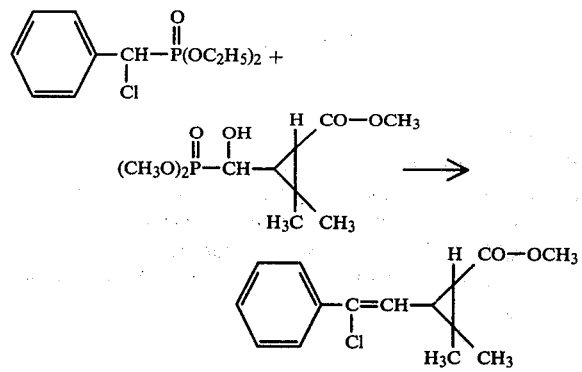

Formula (II) provides a definition of the α-hydroxy-phosphonic acid esters to be used as starting substances. Preferably, in this formula, $R^3$ represents a $C_1$ to $C_4$ alkyl or phenyl radical, or the two radicals $R^3$ together represent a 2,2-dimethyl-propane-1,3-diyl radical, and $R^1$ represents an optionally halogen-substituted $C_1$ to $C_4$ alkyl radical, a $C_2$ to $C_6$ alkenyl radical, a $C_3$ to $C_6$ cycloalkyl radical which is optionally substituted by halogen, cyano, carbamoyl, $C_1$ to $C_4$ alkyl, ($C_1$ to $C_4$ alkyl)-carbonyl, ($C_1$ to $C_4$ alkoxy)-carbonyl and/or phenoxybenzyloxy-carbonyl (which is optionally substituted by fluorine, cyano, and/or ethinyl), or a benzyl or phenylethyl radical which is optionally substituted by chlorine, or a phenyl radical which is optionally substituted by halogen, $C_1$ to $C_4$ alkyl and/or $C_1$ to $C_4$ alkoxy.

In a particularly preferred group of starting compounds of the formula (II), $R^1$ represents a radical of the general formula

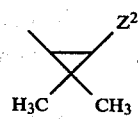

in which $Z^2$ represents a cyano, carbamoyl, acetyl or ($C_1$ to $C_4$ alkoxy)-carbonyl radical, and $R^3$ represents a methyl or ethyl radical.

Examples of compounds of the formula (II) which may be mentioned are: α-hydroxy-3-methyl-benzyl-, α-hydroxy-4-methyl-benzyl, α-hydroxy-3,4-dimethyl-benzyl-, α-hydroxy-4-fluoro-benzyl, α-hydroxy-3-chloro-benzyl-, α-hydroxy-4-chloro-benzyl-, α-hydroxy-3,4-dichlorobenzyl-, α-hydroxy-3-bromo-benzyl-, α-hydroxy-4-bromobenzyl-, α-hydroxy-4-methoxy-benzyl- and α-hydroxy-3,4-dimethoxy-benzyl-phosphonic acid dimethyl esters and diethyl esters; and α-hydroxy-α-(3-methoxycarbonyl-2,2-dimethyl-cycloprop-1-yl)-methanephosphonic acid dimethyl ester and diethyl ester, α-hydroxy-α-(3-ethoxycarbonyl-2,2-dimethyl-cycloprop-1-yl)-methanephosphonic acid dimethyl ester and diethyl ester, α-hydroxy-α-(3-acetyl-2,2-dimethyl-cycloprop-1-yl)-methanephosphonic acid dimethyl ester and diethyl ester and α-hydroxy-α-(3-cyano-2,2-dimethyl-cycloprop-1-yl)-methanephosphonic acid dimethyl ester and diethyl ester.

Some of the starting compounds of the formula (II) have not yet been described in the literature, but they can be prepared by processes which are known in principle.

Thus, substituted α-hydroxy-methanephosphonic acid esters of the formula (II) are obtained by reacting a corresponding oxo compound of the general formula

in which $R^3$ and $R^1$ have the meanings indicated above, with a reducing agent, such as sodium tetrahydridoborate (sodium boranate), optionally using a diluent, such as water or aqueous methanol, at a temperature between $-20°$ and $+50°$ C., preferably between $-10°$ and $+30°$ C., and keeping the pH value between 5 and 8 by adding a buffer, such as sodium hydrogen phosphate (see Chem. Ber. 103 (1970), 2984–2986).

For working up and isolation of the products, the mixture is extracted with a water-immiscible solvent, such as methylene chloride, the organic phase is dried and filtered and the solvent is distilled off from the filtrate under reduced pressure.

Some of the substituted α-oxo-methanephosphonic acid esters of the formula (IV) are not described in the literature. These compounds are obtained by reacting a carboxylic acid chloride of the general formula

in which $R^1$ has the meaning indicated above, with a phosphorus acid ester of the general formula

in which $R^3$ has the meaning indicated above and $R^7$ represents an alkyl radical, in particular a methyl or ethyl radical, at a temperature between $-20°$ and $+150°$ C., preferably between $0°$ and $120°$ C. (see J. Am. Chem. Soc. 86 (1964), 3862–3866 and Methoden der organischen Chemie (Methods of Organic Chemistry) (Houben-Weyl-Muller), 4th Edition, Volume 12.1, page 453, Georg-Thieme-Verlag, Stuttgart 1963).

Compounds of the formulae (V) and (VI) are known. The cyclopropanecarboxylic acid chlorides of the formula (Va) which are not yet known are obtained from known cyclopropane-carboxylic acid esters (see J. Am. Chem. Soc. 89 (1967), 3912–3914; J. Org. Chem. 32 (1967), 3351–3355 Tetrahedron Lett. 1978 1847–1850; and Bull Soc. Chim. Belg. 87 (1978) 721–732 by methods which are in themselves known by first preparing the corresponding cyclopropanecarboxylic acids by hydrolysis, for example by reaction with aqueous-alcoholic potassium hydroxide solution at a temperature between 20° and 100° C. and subsequent acidification, and reacting these acids with halogenating agents, such as thionyl chloride, at a temperature between 20° and 80° C., in accordance with the following equation:

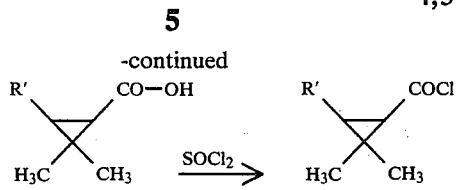

Formula (III) provides a definition of the phosphorus-containing olefinating agents also to be used as starting substances. Preferably, in this formula, $R^2$ represents a chlorine or bromine atom, an alkyl, alkenyl or alkinyl radical with in each case up to 5 carbon atoms, or a phenyl radical which is optionally substituted by halogen, $C_1$ to $C_4$ alkyl, $C_1$ or $C_2$ halogenoalkyl, $C_1$ to $C_4$ alkoxy, $C_1$ and $C_2$ halogenoalkoxy, $C_1$ or $C_2$ (halogeno)alkylenedioxy, $C_1$ to $C_4$ alkylthio and/or $C_1$ or $C_2$ halogenoalkylthio, X represents a chlorine or bromine atom and $Z^1$ represents a radical of the general formula

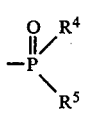

in which $R^4$ and $R^5$ are identical or different and individually represent a $C_1$ to $C_4$ alkoxy or phenoxy radical or together represent a 2,2-dimethyl-propane-1,3dioxy radical.

Examples of compounds of the formula (III) which may be mentioned are: dichloromethanephosphonic acid dimethyl ester and diethyl ester, α-chloro-benzylphosphonic acid dimethyl ester and diethyl ester, α-bromo-benzylphosphonic acid dimethyl ester and diethyl ester, 4-fluoro-, 4-chloro-, 3-chloro-, 3,4-dichloro-, 3-bromo-, 4-bromo-, 3-methyl-, 4-methyl-, 3,4-dimethyl-, 4-methoxy- and 3,4-dimethoxy- α-chloro-benzylphosphonic acid dimethyl esters and diethyl esters, and 4-fluoro-, 3-chloro-, 4-chloro-, 3,4-dichloro-, 3-bromo-, 4-bromo-, 3-methyl-, 4-methyl-, 3,4-dimethyl-, 4-methoxy- and 3,4-dimethoxy- α-bromo-benzylphosphonic acid dimethyl esters and diethyl esters.

Some of the phosphorus-containing olefinating agents of the formula (III) have not yet been described in the literature, but they can be prepared by processes which are known in principle.

α-Chloro- and α-bromo-phosphonic acid esters falling under formula (III) are obtained by reacting α-hydroxy-phosphonic acid esters of the general formula

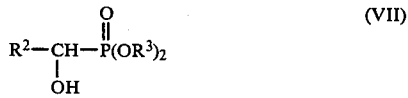

in which $R^2$ and $R^3$ have the meanings indicated above, with a chlorinating agent, such as thionyl chloride, or with a brominating agent, such as dibromotriphenylphosphorane, optionally in the presence of an acid acceptor, such as pyridine, and optionally using a diluent, such as methylene chloride or ethylene chloride, at a temperature between 10° and 100° C. or between −50° and +50° C. (see J. Am. Chem. Soc. 87 (1965), 2777–2778; and Chimia 28 (1974), 656–657).

α-Hydroxy-phosphonic acid esters of the formula (VII) are already known (see DE-OS (German Published Specification) No. 2,827,101).

The process according to the invention for the preparation of alkenes of the formula (I) is preferably carried out using suitable solvents or diluents. Possible solvents or diluents are, in addition to water, virtually any inert organic solvent. These include, as preferences, aliphatic and aromatic, optionally chlorinated hydrocarbons (such as pentane, hexane, heptane, cyclohexane, benzene, toluene, xylene, methylene chloride, ethylene chloride, chloroform, carbon tetrachloride, chlorobenzene and dichlorobenzenes), ethers (such as diethyl ether and dibutyl ether, tetrahydrofuran and dioxane), alcohols, (such as methanol, ethanol, n- and iso-propanol and n-, iso-, sec.- and tert.-butanol) and aprotic polar solvents (such as dimethylformamide and dimethylsulphoxide).

When the reaction is carried out in a two-phase medium, organic solvents which are immiscible with water, such as pentane, hexane, heptane, benzene or toluene, are used, in addition to approximately 50% strength sodium hydroxide solution or potassium hydroxide solution.

Catalysts which are used when the process according to the invention is carried out in multi-phase reaction media are compounds which usually serve as auxiliaries for the phase transfer of reactants in reactions in multi-phase systems. Tetraalkyl- and trialkyl-benzyl-ammonium salts, such as tetrabutylammonium bromide and trimethylbenzyl-ammonium chloride, may be mentioned in particular as such phase transfer catalysts.

The bases customary in carbonyl olefination reactions can be used as bases in carrying out the process according to the invention. Bases which may be mentioned are alkali metal hydroxides (such as potassium hydroxide and sodium hydroxide), alkali metal alcoholates (such as potassium methylate, ethylate, n- and iso-propylate and n-, iso-, sec.- and tert.-butylate and sodium methylate, ethylate, n- and iso-propylate and n-, iso-, sec.- and tert.-butylate), alkali metal hydrides (such as sodium hydride), and alkyl-lithium compounds (such as butyl-lithium). The alkali metal hydroxides and/or alcoholates mentioned are preferably used.

The process according to the invention is carried out using halogen carriers. Possible halogen carriers are, as preferences, compounds of the general formula $$R^8-CX_3 \qquad \text{(VIII)}$$

in which $R^8$ represents a halogen atom, preferably a chlorine or bromine atom, an optionally halogen-substituted alkyl radical, preferably a chloromethyl radical, or an optionally halogen-substituted phenyl radical and X represents a halogen atom, preferably a chlorine or bromine atom.

Examples of the halogen carriers of the formula (VIII) which may be mentioned are: carbon tetrachloride, carbon tetrabromide, hexachloroethane, benzotrichloride and 4-chloro-benzotrichloride. Carbon tetrachloride is particularly preferred.

The process is in general carried out under normal pressure. The reaction temperatures are between −70° and +150° C., preferably between −20° and +50° C.

The starting compounds of the formula (II) and (III) and the halogen carriers of the formula (VIII) are usually employed in approximately equimolar amounts for carrying out the process according to the invention. Two equivalents of base are in general used when the process is carried out in one-phase systems, and in general 5 to 15 times the stoichiometrically required amount is employed when 50% strength alkali metal hydroxide solutions are used as the second phases.

The base and, if appropriate, the catalyst are initially introduced into the reaction vessel in a suitable reaction medium and the starting substances of the formulae (II) and (III) and the halogen carrier are then added simultaneously or successively, if appropriate dissolved in one of the solvents indicated. The mixture is stirred for several hours in order to bring the reaction to completion.

The mixture can be worked up by customary methods. In order to isolate products which can be distilled, a procedure can be followed in which, for example, the solvent is distilled off, the residue is taken up in a water-immiscible solvent, such as ligroin or toluene, the solution is washed with water, dried and filtered and the filtrate is distilled. In order to isolate crystalline products, a procedure can be followed in which the reaction mixture is poured into (ice)-water, if appropriate, and the crystalline product is filtered off, or in which the reaction mixture is washed with water, if the solvent is not water-miscible, dried and filtered and the filtrate is evaporated. Oily products which are difficult to distil can also be obtained in a relatively pure state by the latter method of working up.

The products are characterized by their melting points or boiling points.

Compounds of the formula (I) which can be prepared by the process according to the invention can be used as intermediate products for the preparation of insecticides (see DE-OS (German Published Specification) No. 2,738,150 or U.S. Pat. No. 4,183,944).

PREPARATIVE EXAMPLE (A) (i) α-Halogeno-benzylphosphonic acid esters which were used as starting substances, as phosphorus-containing olefinating agents of the formula (III), could be prepared, for example, as follows:

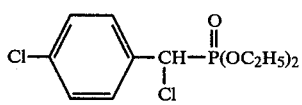

9.2 g (0.0768 mole) of thionyl chloride were added to a mixture of 20.2 g (0.0725 mole) of 4-chloro-α-hydroxy-benzylphosphonic acid diethyl ester, 65 g of methylene chloride and 5.8 g (0.0725 mole) of pyridine at 20° to 40° C. in the course of about 1 hour, while cooling slightly with water. The reaction mixture was then heated under reflux for 3 hours and was subsequently stirred for 12 hours without further heating. The mixture was poured onto about 100 g of ice-water and the organic phase was separated off and dried. After distilling off the solvent, the residue was concentrated under 6 mm Hg and at 45° C. 21 g (97.7% of theory) of 4-chloro-α-chloro-benzyl-phosphonic acid diethyl ester were obtained as a yellow viscous oil with a purity of 98.6% (gas chromatogram) and a refractive index $n_D^{24}$ of 1.5250.

The following compound was obtained analogously:

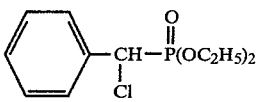 Refractive index: $n_D^{23}$: 1.5117

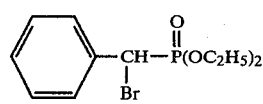

Refractive index: $n_D^{23}$: 1.5117

90 g of bromine, dissolved in 250 ml of methylene chloride, were added dropwise to a solution of 131 g (0.5 mole) of triphenylphosphine in 500 ml of methylene chloride at 30° to 35° C., moisture being excluded. The mixture was subsequently stirred at room temperature for 1 hour, a solution of 122 g (0.5 mole) of α-hydroxy-benzyl-phosphonic acid diethyl ester in 250 ml of methylene chloride was then added dropwise at −20° C. in the course of 1 hour, the mixture was subsequently stirred at −20° C. for 1 hour and 40 g of pyridine, dissolved in 250 ml of methylene chloride, were then added dropwise at −20° C. in the course of one hour. The mixture was subsequently stirred for 20 hours, whereupon the temperature rose slowly to +20° C. The reaction mixture was transferred to a pear-shaped flask and the solvent was distilled off under a waterpump vacuum. The residue was extracted by stirring with one liter of ether and the undissolved triphenylphosphine oxide was filtered off (120 g of triphenylphosphine oxide=86% of theory). The mother liquor was concentrated in vacuo and the residue distilled under a high vacuum. 112 g (72% of theory) of α-bromobenzylphosphonic acid diethyl ester were obtained as a light yellow oil with a boiling point of 110° C./0.01 mm Hg and a purity of 95.9% (gas chromatogram).

The following compound was obtained analogously:

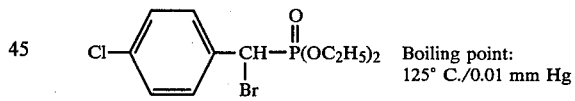 Boiling point: 125° C./0.01 mm Hg (b) (i) Cyclopropanecarboxylic acid chlorides of the formula (Va) which were used as starting substances could be prepared, for example, as follows:

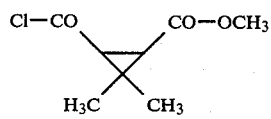

A mixture of 172 g (1 mole) of 3-methoxycarbonyl-2,2-dimethyl-cyclopropane-1-carboxylic acid, 130 g of thionyl chloride, 2 ml of dimethylformamide and 200 ml of methylene chloride was heated to the boiling point under reflux for 4 hours. After distillation of the mixture in vacuo, 135 g (71% of theory) of 3-methoxycarbonyl-2,2-dimethyl-cyclopropane-1-carboxylic acid chloride of boiling point 86° C./15 mbars was obtained.

The following compound was obtained analogously:

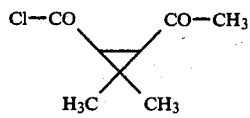

(ii) α-Oxo-phosphonic acid esters of the formula (IV) which were used as starting substances could be prepared, for example, as follows:

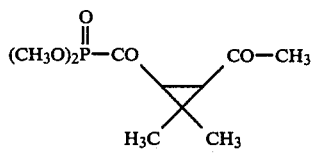

6.5 g (0.05 mole) of trimethyl phosphite were added dropwise to a solution, warmed to 35° to 40° C., of 9 g (0.05 mole) of 3-acetyl-2,2-dimethyl-cyclopropane-1-carboxylic acid chloride in 20 ml of methylene chloride and the reaction mixture was stirred at 15° to 25° C. for 15 hours. After distilling off the solvent in vacuo, 9 g (72% of theory) of α-oxo-α-(3-acetyl-2,2-dimethylcyclopropyl)-methane-phosphonic acid dimethyl ester were obtained.

The following compounds were obtained analogously to the above example:

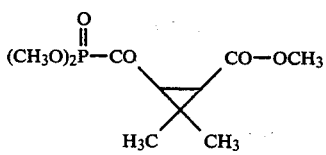

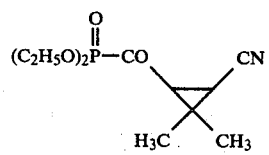

(iii) The α-hydroxy-phosphonic acid esters of the formula (II) which were used as starting substances could be prepared, for example, as follows:

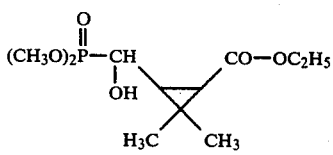

A solution of 56 g (0.2 mole) of α-oxo-α-(3-ethoxycarbonyl-2,2-dimethyl-1-cyclopropyl-methanephosphonic acid dimethyl ester in 100 ml of methylene chloride was added dropwise to a solution, cooled to 0° C., of 2.5 g of sodium tetrahydridoborate in 100 ml of water and the reaction mixture was stirred at 0° C. for a further 90 minutes. The aqueous phase was then separated off from the organic phase and was extracted twice more with methylene chloride. The combined organic phases were dried over sodium sulphate and filtered. The solvent was carefully distilled off from the filtrate under reduced pressure. 40 g (71% of theory) of α-hydroxy-α-(3-ethoxycarbonyl-2,2-dimethyl-1-cyclopropyl)-methanephosphonic acid dimethyl ester were obtained as an oily residue.

The following compounds were obtained analogously:

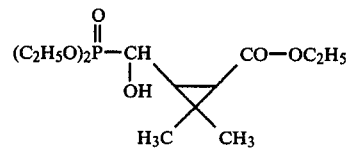

Melting point: 62° C.

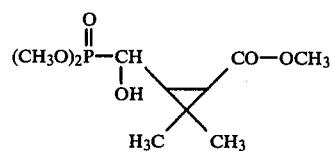

Melting point: 69° C.

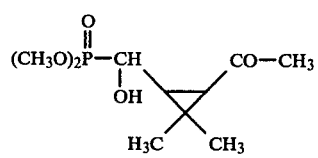

Melting point: 104° C.

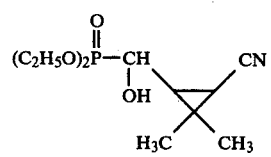

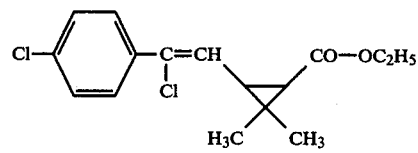

(C)

60 g (0.2 mole) of α-chloro-4-chloro-benzylphosphonic acid diethyl ester were added to a solution, cooled to −10° C., of 21 g (0.4 mole) of sodium methylate in 200 ml of ethanol and 200 ml of tetrahydrofuran in the course of 10 minutes and the mixture was stirred for a further 20 minutes at −10° C. A solution of 58 g (0.2 mole) of α-hydroxy-α-(3-ethoxycarbonyl-2,2-dimethyl-1-cyclopropyl)-methanephosphonic acid dimethyl ester in 31 g of carbon tetrachloride was then added to the mixture at an internal temperature of −10° to 0° C. in the course of 20 minutes. The reaction mixture was stirred at 20° C. for about 15 hours, poured into water and extracted with toluene. The organic phase was washed with water, dried over sodium sulphate and filtered and the filtrate was distilled. 48 g (77% of theory) of 3-(2-chloro-2-(4-chloro-phenyl)-vinyl)-2,2-dimethylcyclopropane-1-carboxylic acid ethyl ester of boiling point 115° C./0.01 mbar were obtained.

3-(2,2-Dichloro-vinyl)-2,2-dimethyl-cyclopropane-1-carboxylic acid ethyl ester, the corresponding methyl ester, n- and iso-propyl ester and n-, iso-, sec.- and tert.-butyl ester and the compounds listed below were also obtained analogously:

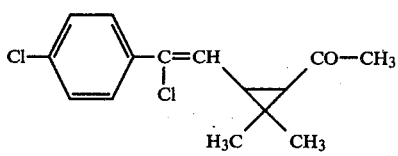

(3-(2-Chloro-2-(4-chloro-phenyl)-vinyl)-2,2-dimethyl-1-cyclopropyl) methyl ketone; boiling point: 90° C./0.01 mbar.

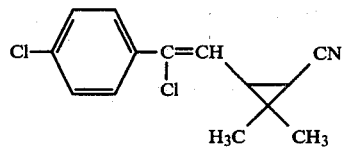

3-(2-Chloro-2-(4-chloro-phenyl)vinyl)-2,2-dimethyl-cyclopropane-1-carboxylic acid nitrile; boiling point: 94° C./0.01 mbar.

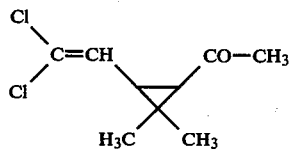

(3-(2,2-Dichloro-vinyl)2,2-dimethyl-1-cyclopropyl) methyl ketone;

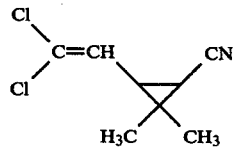

3-(2,2-Dichloro-vinyl)-2,2-dimethyl-cyclopropane-1-carboxylic acid nitrile;

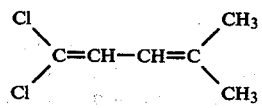

1,1-Dichloro-4-methyl-1,3-pentadiene.

It will be appreciated that the instant specification and examples are set forth by way of illustration and not limitation, and that various modification and changes may be made without departing from the spirit and scope of the present invention.

I claim:

1. In the process for the production of a halogenoalkene of the formula

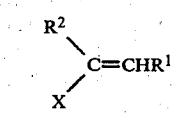

in which $R^1$ is an alkyl, alkenyl, alkinyl, cycloalkyl, cycloalkenyl, aralkyl, aralkenyl or aryl radical, $R^2$ represents a halogen atom, a cyano group, or an alkyl, alkenyl, alkinyl, cycloalkyl, aralkenyl, aryl, alkylcarbonyl, arylcarbonyl, alkoxycarbonyl or aminocarbonyl radical, and X is a halogen atom, in which an α-hydroxy-phosphonic acid ester of the formula

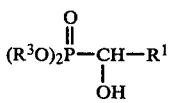

in which $R^3$ each independently is an alkyl or phenyl radical, or the two radicals $R^3$ together are an alkanediyl (alkylene) radical, is reacted with a phosphorus-containing olefinating agent of the formula $$R^2\phantom{xx}\atop{\diagdown}\phantom{x}\atop{CH-Z^1}\phantom{xxx}\atop{\diagup}\atop{X}$$

in which $Z^1$ is the phosphorus-containing radical

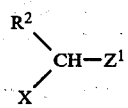

in which $R^4$ and $R^5$ each independently is an alkyl, phenyl, alkoxy or phenoxy radical or together are an alkanedioxy radical, and $R^6$ is an alkyl or phenyl radical, in the presence of a base at a temperature between about −70 and +150° C., the improvement which comprises effecting the reaction in the presence of a halogen carrier of the formula

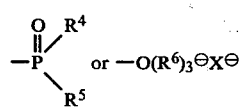

in which $R^8$ is a halogen atom, an optionally halogen-substituted alkyl radical or an optionally halogen-substituted phenyl radical.

2. A process according to claim 1, wherein the reaction is carried out in the presence of a tetraalkyl- or trialkylbenzylammonium salt as catalyst.

3. A process according to claim 1, wherein the reaction is carried out in the presence of a diluent.

4. A process according to claim 3, wherein the diluent is water and an inert organic solvent.

5. A process according to claim 1, wherein the halogen carrier is carbon tetrachloride.

6. A process according to claim 1, in which $R^1$ is

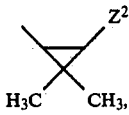

$Z^2$ is a cyano, carbamoyl, acetyl or ($C_1$ to $C_4$—alkoxy)-carbonyl radical, and $R^3$ is a methyl or ethyl radical.

7. A process according to claim 1, in which $R^2$ is a chlorine or bromine atom, an alkyl, alkenyl or alkinyl radical with in each case up to 5 carbon atoms, or a phenyl radical which is optionally substituted by halogen, $C_1$ to $C_4$ alkyl, $C_1$ or $C_2$ halogenoalkyl, $C_1$ to $C_4$ alkoxy, $C_1$ or $C_2$ halogenoalkoxy, $C_1$ or $C_2$ (halogeno)alkylenedioxy, $C_1$ to $C_4$ alkylthio and/or $C_1$ or $C_2$ halogenoalkylthio, X is a chlorine or bromine atom, $Z^1$ is

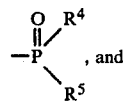, and $R^4$ and $R^5$ each independently is a $C_1$ to $C_4$ alkoxy or phenoxy radical or together are a 2,2-dimethylpropane-1,3-dioxy radical.

8. A process according to claim 1, wherein the base is an alkali metal hydroxide or alkali metal alcoholate.

9. A process according to claim 1, wherein the reaction is carried out at a temperature between about $-20°$ and $+50°$ C.

10. A process according to claim 7, in which the base is an alkali metal hydroxide or alkali metal alcoholate, and the reaction is carried out at a temperature between about $-20$ and $+50°$ C. in the presence of water and an inert organic solvent as diluent and in the presence of a tetraalkyl- or trialkyl-benzyl- ammonium salt as catalyst.

* * * * *

UNITED STATES PATENT AND TRADEMARK OFFICE
CERTIFICATE OF CORRECTION

PATENT NO. : 4,330,482
DATED : May 18, 1982
INVENTOR(S) : Hellmut Hoffmann

It is certified that error appears in the above—identified patent and that said Letters Patent is hereby corrected as shown below:

| | |
|---|---|
| Col. 5, line 15 | After "C", second instance, delete "and" and insert --or-- |
| Col. 8, line 48 | Delete "(b)" and insert --(B)-- |
| Col. 9, line 57 | After "cyclopropyl" insert --)-- |
| Col. 12, line 35 | Should read as follows: |

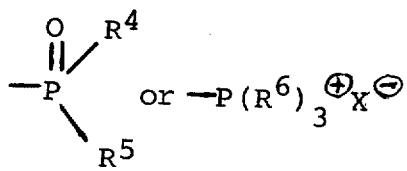

Signed and Sealed this

Seventh Day of December 1982

[SEAL]

Attest:

GERALD J. MOSSINGHOFF

Attesting Officer

Commissioner of Patents and Trademarks